US010221440B2

(12) United States Patent
Tets et al.

(10) Patent No.: US 10,221,440 B2
(45) Date of Patent: Mar. 5, 2019

(54) METHOD FOR DETERMINING THE SENSITIVITY OF MICROORGANISMS TO ANTIMICROBIAL SUBSTANCES

(71) Applicants: Viktor Veniaminovich Tets, Saint-Petersburg (RU); Georgy Viktorovich Tets, Saint-Petersburg (RU)

(72) Inventors: Viktor Veniaminovich Tets, Saint-Petersburg (RU); Georgy Viktorovich Tets, Saint-Petersburg (RU)

(*) Notice: Subject to any disclaimer, the term of this patent is extended or adjusted under 35 U.S.C. 154(b) by 0 days.

(21) Appl. No.: 14/439,717

(22) PCT Filed: May 13, 2013

(86) PCT No.: PCT/RU2013/000394
§ 371 (c)(1),
(2) Date: Apr. 30, 2015

(87) PCT Pub. No.: WO2014/074012
PCT Pub. Date: May 15, 2014

(65) Prior Publication Data
US 2015/0284764 A1 Oct. 8, 2015

(30) Foreign Application Priority Data

Nov. 6, 2012 (RU) .................. 2012147280

(51) Int. Cl.
C12Q 1/18 (2006.01)

(52) U.S. Cl.
CPC .................... *C12Q 1/18* (2013.01)

(58) Field of Classification Search
None
See application file for complete search history.

(56) References Cited

U.S. PATENT DOCUMENTS

| 2,533,088 | A | 12/1950 | Brewer et al. | |
|---|---|---|---|---|
| 5,789,173 | A | 8/1998 | Peck et al. | |
| 6,153,400 | A * | 11/2000 | Matsumura | G01N 21/253 435/283.1 |
| 6,280,946 | B2 * | 8/2001 | Hyldig-Nielsen | C07K 14/003 435/6.12 |
| 6,984,499 | B2 | 1/2006 | Chen et al. | |
| 7,262,021 | B1 | 8/2007 | Taintor | |
| 8,753,875 | B2 | 6/2014 | Frimodt-Moller | |
| 2002/0076742 | A1 | 6/2002 | Chen et al. | |
| 2004/0018585 | A1 | 1/2004 | Crouteau et al. | |
| 2008/0318268 | A1 | 12/2008 | Olson et al. | |
| 2009/0068696 | A1 | 3/2009 | Frimodt-Moller | |
| 2009/0310839 | A1 * | 12/2009 | Katzenelson | C12Q 1/025 382/128 |
| 2011/0269130 | A1 * | 11/2011 | Shi | C12Q 1/18 435/6.11 |
| 2011/0318814 | A1 | 12/2011 | Kshirsagar et al. | |
| 2012/0329675 | A1 | 12/2012 | Olson et al. | |
| 2014/0170671 | A1 | 6/2014 | McGarr et al. | |

FOREIGN PATENT DOCUMENTS

| BY | 7596 U | 10/2011 |
|---|---|---|
| CN | 203904353 U | 10/2014 |
| JP | H1066598 A | 3/1998 |
| RU | 2061032 C1 | 5/1996 |
| RU | 2231554 C2 | 6/2004 |
| RU | 2262533 C2 | 10/2005 |
| RU | 2006111133 A | 10/2007 |
| RU | 69066 U1 | 12/2007 |
| RU | 2319746 C2 | 3/2008 |
| RU | 127749 U1 | 5/2013 |
| RU | 2505813 C1 | 1/2014 |
| WO | 9628570 A1 | 9/1996 |

(Continued)

OTHER PUBLICATIONS

Zhou, Xia, et al. "The vaginal bacterial communities of Japanese women resemble those of women in other racial groups." FEMS Immunology & Medical Microbiology 58.2 (2010): 169-181.*
Ghannoum, Mahmoud A., et al. "Characterization of the oral fungal microbiome (mycobiome) in healthy individuals." PLoS pathogens 6.1 (2010): e1000713.*
Blood Agar, Thermofisher 2008, accessed at: https://tools.thermofisher.com/content/sfs/manuals/IFU1200.pdf.*
Definition of "upon" from the Cambridge Academic Content Dictionary, Cambridge University Press, accessed Mar. 13, 2018 at: https://dictionary.cambridge.org/us/dictionary/english/upon. (Year: 2018).*
Birger M.O., Spravochnik po mikrobiologicheskim i virusologicheskim metodam issledovaniya, Moskva, Medicina, 1973, pp. 177-178 and English Translation thereof.
Epstein S.S., "General model of microbial uncultivability in uncultivated microorganisms", Series: Microbiology Monographs, Springer, (2009), p. 131-150.

(Continued)

Primary Examiner — Robert J Yamasaki
(74) Attorney, Agent, or Firm — Troutman Sanders LLP

(57) ABSTRACT

The invention relates to medicine and to veterinary medicine, and specifically to means for determining the sensitivity of various microorganisms, including bacteria and fungi, to antimicrobial substances. The method for determining the sensitivity of microorganisms to antimicrobial substances comprises taking biological material, incubating microorganisms contained therein on a nutrient medium, introducing an antimicrobial substance to be investigated into the nutrient medium and subsequently assessing the result. A dense, rich nutrient medium is used for cultivating the microorganisms. The antimicrobial substance being investigated is introduced into the nutrient medium prior to cultivation of the microorganisms in a concentration close to the maximum concentration achievable at the location at which the biological material is taken. The sensitivity of the microorganisms to the antimicrobial substance is assessed after the appearance of visible growth of microorganisms in a control culture. Vitamins and/or amino acids, and/or nutritional supplements can be added to the nutrient medium.

14 Claims, No Drawings

(56) References Cited

FOREIGN PATENT DOCUMENTS

| WO | 9918232 A1 | 4/1999 | |
|---|---|---|---|
| WO | WO 2004050675 A1 * | 6/2004 | ............ C12M 23/12 |
| WO | 2009/026920 A1 | 3/2009 | |
| WO | 2011009213 A1 | 1/2011 | |

OTHER PUBLICATIONS

European Communication Pursuant to Rules 70(2) and 70a(2) EPC, Extended/Supplementary European Search Report Issued in EP13853343.5, dated Jun. 23, 2016, 7 pages.

International Search Report and Written Opinion Issued in PCT/RU2013/000394 dated Dec. 12, 2013, 11 pages and English Translation Thereof.

Isenberg H.D. Essential Procedures for Clinical Microbiology, ASM-Press (1998), pp. 208-215, 216-223, and 235-240.

International Search Report and Written Opinion issued in PCT/RU2014/000810, dated Jan. 15, 2015, 12 pages and English Translation Thereof.

International Preliminary Report on Patentability Issued in PCT/RU2014/000810 dated May 31, 2016, 5 pages and English Translation Thereof.

International Preliminary Report on Patentability Issued in PCT/RU2013/000394 dated May 12, 2015, 4 pages and English Translation Thereof.

Lagace-Weins, P.R.S. et al., "Treatment of lower urinary tract infection caused by multidrug-resistant extended-spectrum-β-lactamase-producing *Escherichia coli* with amoxicillin/clavulanate: case report and characterization of the isolate" Journal of Antimicrobial Chemotherapy (2006), 57(6):1262-1263.

Lewis K. et al. "Persisters, biofilms, and the problem of culturability in incultivated microorganisms", Series: Microbiology Monographs, Springer, 2009, p. 181-194.

Opredelenie chuvstvitelnosti rnikroorganizmov k antibakterialnym preparatam, metodicheskie rekomendatsii, klinicheskaya Mikrobiologiya Antimikrobnaya Knimioterapiya (2004), vol. 06:04: p. 311-312 and English Translation thereof titled "Determination of the sensitivity of microorganisms to antibiotics".

European Extended Search Report Issued in EP14866121.8, 9 pages.

US Food and Drug Administration "Chapter 3: types of Devices and predictive device" In: "Guidance for Industry and for FDA Reviewers Guidance on Review Criteria for Assessment of Antitiicrobial Susceptibilitiy Devices" (1991), US Department of Health and Human Services, Washington DC USA, XP055364834, pp. 1-22.

European Communication issued by the European Patent Office in European Patent Application No. 13853343.5, dated Nov. 13, 2017, 5 pages total.

International Preliminary Report on Patentability and Written Opinion (including translation) issued by the International Searching Authority in International Patent Application No. PCT/RU2016/000383, dated Dec. 26, 2017, 9 pages total.

International Search Report (including translation) issued by the International Searching Authority in International Patent Application No. PCT/RU2016/000383, dated Oct. 20, 2016, 3 pages total.

Ellner, P.D. et al., "A New Culture Medium for Medical Bacteriology" The American Journal of Clinical Pathology (1996) vol. 45, No. 4, pp. 502-504.

Poliak, M.C. et al., "Pitatelnye Sredy Dlia Meditsinskoi Mikrobiologii" St. Petersburg (2002), 80 pages total.

Korotchenko, H.M. et al., "Izuchenie Ustoichivosti Violuratnykh Kompleksov Nekotorykh D-i F-metallov" Zhurnal Neorganicheskoi Khimii (2012) vol. 57, No. 1, pp. 141-147.

Dong, Q. et al., "The Microbial Communities in Male First Catch Urine are Highly Similar to Those in Paired Urethral Swab Specimens" (2011) PLoS One vol. 6, Issue 5, e19709, pp. 1-5.

Oliver, J.D., "Recent Findings on the Viable but Nonculturable State in Pathogenic Bacteria" (2010) FEMS Microbiology Reviews (2010) vol. 34, pp. 415-425.

Petrosino, J.F. et al., "Metagenomic Pyrosequencing and Microbial Identification" Clinical Chemistry (2009) vol. 55, No. 5, pp. 856-866.

European Communication Pursuant to Article 94(3) EPC issued by the European Patent Office in European Application No. 13 853 343.5, dated May 24, 2018, 5 pages total.

Communication issued by the United States Patent and Trademark Office in U.S. Appl. No. 15/039,966, dated Jun. 5, 2018.

Funk, D.J. et al., "Antimicrobial Therapy for Life-Threatening Infections: Speed is Life" Critical Care Clinics (2011) vol. 27 pp. 53-76.

Hellenkamp, K. et al., "Early Pneumonia and Timing of Antibiotic Therapy in Patients After Nontraumatic Out-of-Hospital Cardiac Arrest" Critical Care (2016) vol. 20, No. 31, 10 pages total.

* cited by examiner

METHOD FOR DETERMINING THE SENSITIVITY OF MICROORGANISMS TO ANTIMICROBIAL SUBSTANCES

CROSS-REFERENCE TO RELATED APPLICATIONS

This application is a U.S. National Phase of International Patent Application No. PCT/RU2013/000394, filed May 13, 2013, which claims priority to Russian Patent Application No. 2012147280, filed Nov. 6, 2012.

TECHNICAL FIELD

The invention relates to means for determining the sensitivity of various microorganisms (including bacteria and fungi) that cause diseases in humans, animals and plants and also damage food and industrial products to antimicrobial substances—antibiotics and antiseptics—and can be used mainly in medicine as well as in veterinary medicine, agriculture and industry.

BACKGROUND ART

One of the most serious problems of contemporary medicine, veterinary medicine, plant production and industry lies in the activity of various microorganisms, especially bacteria and fungi, that cause diseases and damage of products. The fight against bacteria and fungi remains insufficiently effective due to great variability of microorganisms that leads to the emergence of resistant forms, the inability to grow significant amounts of microbes and the absence of effective methods for choosing an antimicrobial means. For this reason during the first 3-4 days the antimicrobial preparations are used empirically. In medicine and veterinary medicine various broad-spectrum antibiotics are used in such situations, but the number of such antibiotics is limited, which leads to quick formation and propagation of resistance towards such antibiotics, resulting in complications and, at times, even death in medicine and veterinary medicine, and irreversible damage of food and industrial products.

In this regard a quick and precise assessment of sensitivity of microorganisms to antimicrobial preparations—antibiotics and antiseptics—constitutes an urgent and yet unsolved problem.

Known methods of determining the sensitivity to antimicrobial preparations comprise preliminary isolation of pure culture of a microorganism and identification of said pure culture.

However, the isolation of pure culture of microorganisms has some negative implications, most notably the loss of time (48-96 hours). Furthermore, if two or more microorganisms are present, some of them will not be isolated as a pure culture. It should also be noted that some "not-yet-cultivated" microbes cannot be isolated at all, and according to various sources such microbes can constitute up to 90-95% of all microbes.

The difficulties of dealing with such microbes consist mainly in the absence of methods for isolating, growing and identifying these microbes. The latter is due to the way the life of bacteria is organized within microbial communities (biofilms), which determines great interdependence between microorganisms. These conditions as yet cannot he recreated in a laboratory, see Lewis K., Epstein S. S. Persisters, biofilms, and the problem of culturability in incultivated microorganisms. In Series: Microbiology Monographs. Steinbuchel A. (ed.). Berlin/Heidelberg: Springer; 2009, pp. 181-194, Epstein S. S. General model of microbial uncultivability in uncultivated microorganisms. In Series: Microbiology Monographs. Steinbuchel A. (ed.), Berlin/Heidelberg: Springer; 2009, pp. 131-150.

A known method comprises applying antimicrobial substances onto strips in a certain way, see Isenberg H. D. Essential Procedures for clinical Microbiology, ASM-Press, 1998, USA, pp. 235-240. The serial dilution method comprises inoculation of a pure culture onto a special-purpose fluid medium Muller Hinton with the addition of antimicrobial substances (antibiotics) in varying concentrations, see Isenberg H. D. Essential Procedures for clinical Microbiology, ASM-Press 1998, USA, pp. 216-223. Some methods of semi-automatic determination of sensitivity to antibiotics employ detection by means of special-purpose equipment (e.g. Vitec 2 BioMerie panels). However, the method also uses preliminary isolation of pure culture of the assumed causative agent with subsequent exposure thereof in wells of the panel. Genetic methods allow detecting certain studied genes of antibiotic resistance among identified bacteria or even directly in the pathologic material. Said method is relatively quick, however it does not yet allow fully evaluating the sensitivity to antimicrobial preparations. This is due to the fact that many microorganisms have not been studied yet and therefore there are no data on their genome or the genes of antibiotic resistance thereof. Secondly, even among known and cultivable bacteria the resistance to a specific antimicrobial preparation can be encoded by completely different genes, many of which remain unstudied.

Another known method for determining the sensitivity of microorganisms to an antimicrobial substance comprises taking biological material and isolating, a pure culture of the microorganism. In order to isolate a pure culture, the biological material is inoculated in nutrient media that provide favorable conditions for the growth of a particular microorganism that presumably causes diseases or damage of products and materials. If the microorganism growth is successful, the microorganism is identified. Then the sensitivity thereof to an antimicrobial substance is determined by means of inoculation of isolated pure culture of the microorganism on Muller Hinton nutrient medium or a similar non-rich medium that does not contain the antimicrobial substance, followed by the placement of paper disks saturated with various antimicrobial substances upon the surface of the nutrient medium inoculated with microorganisms, and incubation of the microorganisms in the nutrient medium in the presence of the antimicrobial substances being investigated with subsequent assessment of the results, see Isenberg H. D. Essential Procedures for clinical Microbiology, ASM-Press, 1998, USA, 1998, pp. 208-215.

Yet another known method for determining the sensitivity of microorganisms to an antimicrobial substance (antibiotics) comprises taking biological material, cultivating the microorganisms contained therein on a nutrient medium that does not contain the antimicrobial substance, introducing the antimicrobial substance being investigated into the medium and subsequently assessing the results; the biological material is cultivated in sugar broth for at least two hours, then standard disks containing the antibiotics being investigated are introduced and the medium is further incubated for at least two hours, the result is assessed by the degree of opacity of the sample contents: the less the opacity, the higher the sensitivity of the microorganisms to the antibacterial substances, see RU 2262533C2.

The disadvantages of this method, which has been taken as a prototype of the present invention, consist in the following:

fairly low precision of the results' assessment, because the reduction of opacity of the sample contents can be caused by inhibition of growth of microbes other than the causative agents, the sensitivity of which to an antimicrobial substance is investigated;

since the biological material is for a long time (>2 hours) contained in a nutrient medium that does not include an antimicrobial substance, the selective growth of some microorganisms changes the overall composition of microorganisms as compared to the original material, which drastically distorts the results of the study;

introducing the antimicrobial substance to the nutrient medium on standard disks is reasonable only for isolated pure cultures, because the reference values of areas of inhibition of microorganism growth, which would allow evaluating their sensitivity and resistance to a particular antimicrobial substance, are defined only for pure cultures. In said method the pure culture of the microorganism is not isolated, thus making it impossible to take into account the microorganism's specifics or the maximum possible concentration of the antimicrobial substance at the place where the biological material is taken;

using a non-rich fluid nutrient medium does not enable growth of the majority of microorganisms.

It is an object of the present invention to provide a solution for increasing the precision of determining the sensitivity of microorganisms to an antimicrobial substance.

SUMMARY OF THE INVENTION

According to the invention the method for determining the sensitivity of microorganisms to antimicrobial substances comprises taking biological material, incubating microorganisms contained therein on a nutrient medium, introducing an antimicrobial substance to be investigated into the nutrient medium and subsequently assessing the result, wherein a rich nutrient solid medium is used for cultivating the microorganisms, the antimicrobial substance being investigated is introduced into the nutrient medium prior to cultivation of the microorganisms in a concentration dose to the maximum concentration achievable at the location where the biological material is taken, also a control inoculation of microorganisms is carried out on a nutrient medium that does not contain the antimicrobial substance, and wherein the sensitivity of the microorganisms to the antimicrobial substance is assessed after the appearance of visible growth of microorganisms in a control culture; the rich nutrient solid medium that is used for incubating bacteria is embodied as *Brucella* Agar medium or Columbia Agar medium, whereas Sabouraud medium is used for incubating fungi; human blood serum or animal blood serum and/or red blood cells can be added to the nutrient medium; vitamins and/or amino acids, and/or nutritional supplements can be added to the nutrient medium; the nutrient medium can additionally contain microorganisms that promote the growth of microorganisms being investigated during co-cultivation thereof: antibacterial preparations can be added to the nutrient medium used for cultivating fungi; antifungal preparations can be added to the nutrient medium used for cultivating bacteria; incubation of microorganisms can be performed in aerobic conditions; incubation of microorganisms can be performed in anaerobic conditions; incubation can be performed in the presence of one or several supplementary antimicrobial substances; the nutrient medium can be placed into Petri dishes; the nutrient medium can be placed into a plate made of plastic or paper.

The applicant has not found any technical solutions identical to the claimed solution, which enables to conclude that the invention conforms to the patentability criterion "Novelty" (N).

The claimed invention differs from the prototype and other known analogous solutions in that it is not limited to determining the sensitivity of certain microorganisms that are characteristic of a particular disease of humans, animals or plants, or damage and spoilage of products and materials.

The claimed method is based on a novel principle, which consists in trying to grow (whenever possible) all microorganisms contained within the collected material and then determining which antimicrobial substance is the most effective and efficient at inhibiting the totality of said microorganisms, without trying to actually or supposedly identity these microorganisms as is the case with the known methods.

In other words, to provide a solution for fighting the source of diseases and damage of products and materials one does not need to know what the source is, it is enough to know which substance makes it possible to eliminate or reduce the harmful effects of said source.

Implementation of the features of the invention provides the object of the invention with the abovementioned fundamentally new property and corresponding technical result, winch consists in significantly increased precision of the investigation results.

A rich nutrient solid medium allows growing the maximum number of different microorganisms contained within the sample. It is important to introduce the antimicrobial substance to be investigated into the nutrient medium before the cultivation of microorganisms begins. This distinction prevents changes in the overall composition of microorganisms during the cultivation process as compared to the original material. It is important to introduce the antimicrobial substance in a concentration that is close to the maximum concentration achievable at the location at which the biological material is taken and not in an arbitrary concentration as is the case with using standard disks to introduce the antimicrobial substance. The assessment of sensitivity of microorganisms is not based on the level of opacity of the sample contents, which could be related to the inhibition of microbes that are not pathogenic (harmful); instead, it is based on the appearance of visible growth of microorganisms in a control culture.

The essentially novel circumstance a the claimed method consists in that the addition of certain microorganisms into the nutrient medium and joint cultivation thereof together with disease-causing agents can promote the growth of even those microorganisms in the sample that are otherwise not-cultivated.

In applicant's opinion, the abovementioned new properties of the claimed method enable to conclude that the method conforms to the patentability criterion "Inventive Step" (IS).

BRIEF DESCRIPTION OF THE DRAWINGS

The invention is further explained by way of detailed description of examples of its embodiments, without reference to any drawings.

PREFERRED EMBODIMENT

The implementation of the method is further explained by means of the examples provided below.

EXAMPLE 1

Express determination a bacteria sensitivity to azithromycin while inoculating material obtained from a patient suffering from a urinary system infection.

The biological material was taken: urine of a patient suffering from cystitis.

Nutrient medium: solid, rich—*Brucella* Agar medium enriched with horse serum and human and sheep red blood cells. Azithromycin was added to the medium beforehand in maximum concentration sufficient in urine—4 µg/ml.

The material was inoculated in Petri dishes in the amount of 0.2 ml. Analogous medium and cultivation conditions were used for control purposes (in the control culture). The culture was incubated at temperature of 37° C.

Results of the investigation. After 4-6 hours of growth at temperature of 37° C. the formation of lawn was observed in the control culture.

In other words, the growth of a large number of different unrelated bacteria was observed on rich nutrient solid medium in the control culture, whereas no growth of said bacteria could be observed in the presence of azithromycin, which can thus be successfully used for treating this particular patient. There was no need to identity specific causative agents or isolate the pure culture. The answer necessary for prescribing an antibiotic was ready in 4 hours.

EXAMPLE 2

Express determination of bacteria sensitivity to ampicillin while inoculating material obtained from an animal (a dog) with a wound infection.

The method was carried out similarly to the way described in example 1.

Material to be investigated: secretion from the wound.

Nutrient medium: Columbia Agar medium enriched with horse serum and sheep red blood cells, vitamins and amino acids. Ampicillin was added to the medium in maximum concentration achievable at the location where the material was taken—1 µg/ml.

Material taken from the wound was plated using a swab on the medium in a Petri dish. Same medium and cultivation conditions (without ampicillin) were used for control purposes.

The culture was incubated at temperature of 37° C.

Results of the investigation. After 4-6 hours of growth at temperature 37° C. the formation of lawn was observed in the control culture. No bacterial growth was observed in the dish with ampicillin.

In other words, the growth of a large number of different unrelated bacteria was observed in solid rich medium, whereas no growth at said bacteria could be observed in the presence of ampicillin, which can thus be successfully used for treating this particular animal. There was no need to identity specific causative agents or isolate the pure culture. The answer necessary for prescribing an antibiotic was ready in 4 hours.

EXAMPLE 3

Choosing an antiseptic for eliminating household mold obtained from exposed plaster.

Material to be investigated: pieces of exposed plaster showing evidence of mold growth. A suspension of the plaster (0.5 g) in 1.0 ml of isotonic sodium chloride solution was prepared.

Nutrient medium: Sabouraud Agar medium enriched with mineral components, placed into three Petri dishes. The following preparations were added to the medium beforehand: the first dish—antiseptic Multicide, a hydrazine derivative of polyguanidine, solvent—water, in final concentration of 0.5% (which can be achieved without altering the properties of plaster and other similar materials—color, odor and mechanical characteristics); the second dish—antiseptics; Teflex—a complex of guanidine copolymers. Solvent—water (0.5%); the third dish—control without any antiseptics.

The material was plated using an inoculation loop.

The inoculations were cultivated at 30° C. The results were analyzed after 4, 6, 12, 20, 24 and 48 hours after the inoculation.

Results. After 6 hours of cultivation the growth was observed in the control dish and in the dish that contained agar with Teflex preparation. No growth was observed in dishes with Multicide. The mold turned out to be resistant to Teflex preparation and sensitive to Multicide preparation. There was no need to identify specific causative agents or isolate the pure culture. The answer required for choosing an antiseptic was ready in 6 hours.

EXAMPLE 4

Choosing an antibiotic for treating respiratory diseases.

Material to be investigated—sputum of a patient.

Nutrient medium: *Brucella* Agar medium enriched with horse serum and human red blood cells. *Haemophilus influenzae* bacteria were added to the medium, which cause respiratory diseases and promote the growth of another pathogen—*Streptococcus pneumonia*—that is very poorly cultivated under normal conditions. Levofloxacin was also added to the medium in the maximum concentration achievable in sputum—10 µg/ml.

Freshly collected sputum of the patient was diluted fivefold in an isotonic solution of sodium chloride, plated in the amount of 0.2 ml per dish using a spreader and incubated at a temperature of 37° C. The results were analyzed after 4, 6, 12, 20 and 24 hours after the inoculation.

Results. After 4 hours of growth at temperature of 37° C. the formation of lawn was observed in the control culture. In the medium that contained levofloxacin: after 4, 6, 12, 20 and 24 hours there was no sign of growth. Microscopic investigation showed the following: after 24 hours there were more than 12 morphotypes of microorganisms on smears prepared from bacteria grown in the control sample; whereas in the medium that contained levolioxacin there was no growth.

Thus, the provided technology allows quickly (within 4 hours) choosing an antibiotic that will inhibit the growth of all potential causative agents of this pathology, including those that are practically not-cultivated under normal conditions. There was no need to identity specific causative agent or isolate the pure culture.

EXAMPLE 5

Express determination of sensitivity to a mixture of antibiotics, namely gentamicin (mainly affects aerobic bacteria) and metronidazole (active against anaerobic bacteria and microaerophils), while inoculating material obtained from a patient suffering from a disease of periodontium.

Material to be investigated: freshly collected secretion of subgingival space.

Nutrient medium: Columbia Agar medium enriched with sheep red blood cells and horse serum was used for cultivation in aerobic conditions. Anaerobic microorganisms were detected using Schaedler Agar containing sheep red blood cells and serum. 2 and bioties were added to the medium: gentamicin (active against a wide range of aerobes) and metronidazole that selectively affects anaerobic bacteria. Medium in dishes 1 and 1a contains gentamicin; medium in dishes 2 and 2a contains metronidazole; medium in dishes 3 and 3a contains gentamicin and metronidazole; dishes 4 and 4a contain only the nutrient medium (control).

The secretion of subgingival space was diluted fivefold using isotonic solution of sodium chloride and plated in the amount of 0.05 ml per dish using a spreader. The inoculations were cultivated: in the case of aerobes (dishes 1-4)—in a regular air bath, and in the case of anaerobes (dishes 1a-4a) in an air bath in anaerobic conditions at 37° C. for 48-72 hours. Gas-generating sets were used to create anaerobic conditions. The results were analyzed after 4, 8, 12, 20, 24 and 48 hours after the inoculation (anaerobic bacteria are characterized by lengthy growth).

Results. After 4 hours of growth in aerobic conditions and 8 hours of growth in anaerobic conditions at temperature of 37° C. the formation of lawn was observed in the control culture. In aerobic conditions in the test dish 3 that contained gentamicin and metronidazole there was no growth throughout the whole observation period. In anaerobic conditions in the test dish 3a that contained gentamicin and metronidazole there was no growth after 8 hours. Microbial growth was observed in dishes 1, 1a, 2 and 2a. The obtained data show that the mixture of gentamicin and metronidazole was effective and that resistant clones emerge when the preparations are used separately.

Therefore the claimed method, as opposed to the prototype thereof, allows assessing the sensitivity to a mixture of antimicrobial preparations.

EXAMPLE 6

Express determination of the sensitivity of fungi that cause diseases of plants (powdery mildew) to antifungal preparations.

Material to be investigated: wipe sampling of isotonic solution of sodium chloride taken from affected areas of a leaf of a plant that has indications of fungi growth.

Nutrient medium: Sabouraud Agar medium enriched with mineral components, placed into a plate with six wells. in order to prevent the growth of bacteria, gentamicin was added to the agar in the amount of 0.01 mg/l. The antifungal preparations to be investigated were also added to the medium: 1st well—propiconazole, in final concentration of 1%; 2nd well—nystatin (0.4 mg/l); 3rd well—control without any antifungal preparations.

1.0 ml of isotonic solution a sodium chloride was washed from 4 cubic cm of the affected area. The material was plated using an inoculation loop.

The inoculations were cultivated at 30° C. The results were analyzed after 6, 8, 12, 20, 24 and 48 hours after the inoculation.

Results. After 8 hours of cultivation the growth was observed in the control well and in the well that contained agar with nystatin preparation. No growth was observed in the well with propiconazole. The mold turned out to be resistant to nystatin preparation. There was no need to identify specific causative agent or isolate the pure culture. The answer required for choosing an antifungal preparation was ready in 8 hours.

INDUSTRIAL APPLICABILITY

The invention can be implemented by means of known materials and equipment. In applicant's opinion, this enables to conclude that the invention conforms to the criterion "Industrial Applicability" (IA).

The invention claimed is:

1. A method for determining the sensitivity of microorganism(s) in a sample to one or more antimicrobial compounds comprising:
   (a) (i) incubating a first portion of the sample on a control medium, wherein said control medium is a solid nutrient medium, and (ii) incubating a second portion of the sample under the same conditions on an antimicrobial medium, wherein said antimicrobial medium is identical to the control medium and further comprises the one or more antimicrobial compounds, wherein said one or more antimicrobial compounds are introduced into the antimicrobial medium prior to adding the sample to the antimicrobial medium,
   (b) upon the appearance of a lawn of microorganisms on the control medium, comparing the extent of microorganism growth on the antimicrobial medium with the extent of microorganism growth on the control medium, and
   (c) determining (i) that the microorganism(s) in the sample are sensitive to the one or more antimicrobial compounds if there is no visible microorganism growth on the antimicrobial medium or (ii) that at least one microorganism in the sample is resistant to the one or more antimicrobial compounds if there is a visible microorganism growth on the antimicrobial medium,
   wherein the sample is from a human or animal subject,
   wherein the concentration of each of the one or more antimicrobial compounds in the antimicrobial medium is approximately the maximum concentration achievable in a tissue or body fluid from which the sample was obtained, and
   wherein said control medium is an enriched medium that allows growth of a wide variety of different microorganisms present in the sample.

2. The method of claim 1, wherein the medium is *Brucella* Agar medium, or Columbia Agar medium, or Sabouraud medium.

3. The method of claim 1, wherein the medium comprises blood serum and/or red blood cells.

4. The method of claim 1, wherein the medium comprises vitamins and/or amino acids, and/or nutritional supplements.

5. The method of claim 1, wherein the control medium and the antimicrobial medium comprise microorganisms that promote growth of one or more microorganisms in the sample.

6. The method of claim 1, wherein the incubation in step (a) is performed in aerobic conditions.

7. The method of claim 1, wherein the incubation in step (a) is performed in anaerobic conditions.

8. The method of claim 1, wherein the medium is placed in a Petri dish.

9. The method of claim 1, wherein the medium is placed in a plate made of plastic or paper.

10. The method of claim 1, wherein the incubation in step (a) is conducted for 4-12 hours.

11. The method of claim 1, wherein the medium comprises agar.

12. The method of claim 10, wherein the incubation in step (a) is conducted for 4-6 hours at 37° C. in aerobic conditions.

13. The method of claim 10, wherein the incubation in step (a) is conducted for 8-12 hours at 30° C. in aerobic conditions.

14. The method of claim 10, wherein the incubation in step (a) is conducted for 8-12 hours at 37° C. in anaerobic conditions.

\* \* \* \* \*